(12) United States Patent
Miller et al.

(10) Patent No.: US 8,227,647 B2
(45) Date of Patent: Jul. 24, 2012

(54) METHOD OF PRODUCING ALCOHOLS

(75) Inventors: Jorge Miller, Houston, TX (US); Luisa Kling Miller, Houston, TX (US)

(73) Assignee: Sajet Development LLC, Houston, TX (US)

( * ) Notice: Subject to any disclaimer, the term of this patent is extended or adjusted under 35 U.S.C. 154(b) by 59 days.

(21) Appl. No.: 12/927,936

(22) Filed: Nov. 30, 2010

(65) Prior Publication Data

US 2011/0130597 A1    Jun. 2, 2011

Related U.S. Application Data

(60) Provisional application No. 61/336,962, filed on Jan. 28, 2010, provisional application No. 61/283,167, filed on Nov. 30, 2009.

(51) Int. Cl.
*C07C 29/48* (2006.01)
*C07C 27/16* (2006.01)

(52) U.S. Cl. .............. 568/911; 568/910; 568/910.5

(58) Field of Classification Search ............. 568/911, 568/910, 910.5
See application file for complete search history.

(56) References Cited

U.S. PATENT DOCUMENTS 5,354,916 A * 10/1994 Horvath et al. ............... 568/893

* cited by examiner

*Primary Examiner* — Elvis O Price
(74) *Attorney, Agent, or Firm* — McDermott Will & Emery LLP

(57) ABSTRACT

A method comprising reacting an alkane gas with a halogen gas in a halogenations reactor to form a halogenation reaction product mixture comprising alkane halide and hydrogen halide mixture; mixing the halogenations reaction product mixture with a countercurrent flow of a metal organic salt thereby forming an extractor product mixture of a metal halide, organic salt, and organic acid separating the organic ester and organic acid mixture from the metal halide; oxygenating the metal halide to form a metal oxide and halide containing gasses; separating the metal oxide from the halide containing gasses; mixing the metal oxide with water to form a metal oxide slurry; mixing the metal oxide slurry with a countercurrent flow of the organic ester and organic acid mixture to form a raw product comprising alkanol, a metal organic salt is provided.

19 Claims, 1 Drawing Sheet

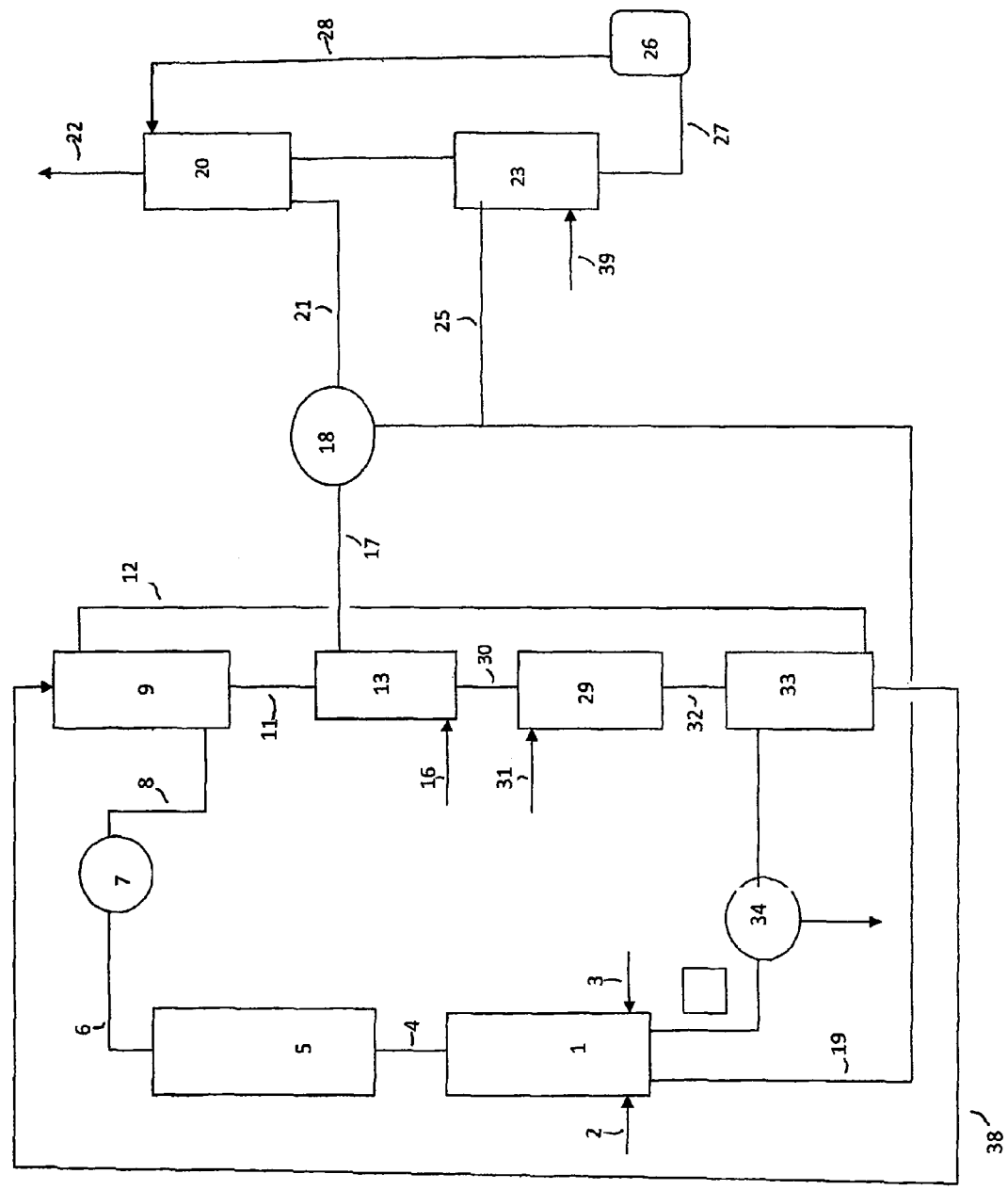

METHOD OF PRODUCING ALCOHOLS

RELATED APPLICATIONS

This application claims priority to U.S. Provisional Application Nos. 61/283,167 filed on Nov. 30, 2009; and 61/336,962, filed on Jan. 28, 2010, the disclosures of which are each incorporated herein by reference.

FIELD OF INVENTION

The invention relates to a method of making alcohols, and more specifically alkanols, from alkanes, and more specifically from alkane halides.

BACKGROUND OF THE INVENTION

Alcohols are industrially produced from direct hydration of alkenes, such as ethylene, or from cracking of appropriate fractions of distilled (or fractionated) crude oil. While demands for alcohols, and especially for ethanol, continue to increase, crude oil reserves continue to be depleted. Moreover, the processes of alkene hydration and fractionation and cracking of crude oil are themselves energy intensive processes.

There remains a need therefore, for a method of producing alcohols from more readily available starting materials and for a process which does not require the energy input necessary for current industrial alcohol production.

SUMMARY OF THE INVENTION

The invention provides a method of making alcohols. More specifically, the inventive method comprises reacting an alkane gas with a halogen gas in a halogenation reactor to form a halogenation reaction product mixture comprising alkane halide and hydrogen halide mixture; contacting the halogenation reaction product mixture with a metal organic salt thereby forming an extractor product mixture of a metal halide, organic ester, and organic acid; separating the organic ester and organic acid mixture from the metal halide; oxygenating the metal halide to form a metal oxide and halide containing gasses; separating the metal oxide from the halide containing gasses; mixing the metal oxide with water to form a metal oxide slurry; mixing the metal oxide slurry with a countercurrent flow of the organic ester and organic acid mixture to form a raw product comprising alkanol, a metal organic salt.

BRIEF DESCRIPTION OF THE DRAWINGS

The drawing illustrates an exemplary form of the invention; it being understood, however, that this invention is not limited to the precise arrangements and instrumentalities shown in the drawing.

FIG. 1 is a schematic diagram of one embodiment of the inventive process.

DETAILED DESCRIPTION OF THE INVENTION

The invention is a method for making alcohols. The invention is a method for producing organic alcohols, including for example, methanol, ethanol, propanol, and combinations thereof.

In one embodiment, the instant invention provides a method comprising: reacting an alkane with a halogen gas in a halogenations reactor to form a halogenation reaction product mixture comprising alkane halide and hydrogen halide mixture; contacting the halogenation reaction product mixture with a metal organic salt thereby forming an extractor product mixture of a metal halide, organic salt, and organic acid; separating the organic ester and organic acid mixture from the metal halide; oxygenating the metal halide to form a metal oxide and halide containing gasses; separating the metal oxide from the halide containing gasses; mixing the metal oxide with water to form a metal oxide slurry; mixing the metal oxide slurry with a countercurrent flow of the organic ester and organic acid mixture to form a raw product comprising alkanol, a metal organic salt.

Alkanes useful in various embodiments of the inventive method may be selected from the group consisting of C1-C20 alkanes, including most preferably, methane, ethane, propane, butane and mixtures thereof. All combinations and subcombinations of such alkanes are included and disclosed herein. For example, the alkanes may comprise a mixture of methane and ethane; or in the alternative, a mixture of methane and propane; or in the alternative, a mixture of ethane and butane. In the alternative, the alkane may comprise only a single alkane. For example, the alkane may comprise methane with no other alkane component; or in the alternative, the alkane may comprise ethane with no other alkane component; or in the alternative the alkane may comprise propane with no other alkane component.

Halogen gasses useful in various embodiments of the invention may be selected from the group consisting of chlorine gas, bromine gas, iodine gas, and combinations thereof. All combinations and subcombinations of such halogen gasses are included and disclosed herein. For example, the halogen gasses may comprise a mixture of chlorine and bromine gasses; or in the alternative the halogen gasses may comprise a mixture of chlorine and iodine gasses. In the alternative, the halogen gas useful in the halogenations step of the inventive method may comprise only a single halogen gas. For example the halogen gas may be bromine gas; or in the alternative, the halogen gas may be chlorine gas. The halogen gas or gasses used in the halogenation reactor may be supplied directly into the halogenations reactor, as for example, by injection through a dedicated supply line. Alternatively, the halogen gas or gasses used in the halogenation reactor may be formed in situ in the halogenation reactor.

Metal organic salts useful in the inventive method may be selected from the group consisting of metal formate, metal acetate, metal benzoate, and combinations thereof. The metal of the metal organic salt in various embodiments of the inventive method may be selected from Magnesium, Zinc, and combinations thereof. All combinations and subcombinations of the metal organic salts are disclosed and included herein. For example, the metal organic salt may be magnesium formate, zinc acetate, magensium benzoate, zinc dichlorobenzoate, zinc dichloroacetate, or any combination of two or more of the foregoing.

In one embodiment of the inventive method, the alkane is methane, the metal organic salt is magnesium formate, the halide gas is bromine gas, and the alkanol is methanol.

In an alternative embodiment, the invention provides a method of making alkanols except that the halogen gas is chlorine gas.

In an alternative embodiment, the invention provides a method of making alkanols except that the halogen gas is a mixture of bromine and chlorine gasses.

In an alternative embodiment, the invention provides a method of making alkanols except that the alkane is ethane.

In an alternative embodiment, the invention provides a method of making alkanols except that the alkane is propane.

In an alternative embodiment, the invention provides a method of making alkanols except that the alkane is butane.

In an alternative embodiment, the invention provides a method of making alkanols except that the alkane is a mixture of methane and ethane.

In an alternative embodiment, the invention provides a method of making alkanols except that the metal organic salt is magnesium acetate.

In an alternative embodiment, the invention provides a method of making alkanols except that the metal organic salt is magnesium benzoate.

In an alternative embodiment, the invention provides a method of making alkanols except that the metal organic salt is zinc benzoate.

In an alternative embodiment, the invention provides a method of making alkanols except that the metal organic salt is magnesium acetate.

In an alternative embodiment, the invention provides a method of making alkanols except that the metal organic salt is zinc formate.

The various steps of the inventive method may be conducted in any appropriate reactor. For example, the step of oxygenating the metal halide may occur in a fluidized bed reactor. In some embodiments of the inventive method the step of contacting the halogenation reaction product mixture with a metal organic salt occurs in a column packed with an inert packing material. Any one or more inert materials as are known in the art may be used in the step of contacting the halogenations reaction product mixture with a metal organic salt may be used, including for example Berl saddles. In some embodiments of the inventive method, the step of contacting the halogenation reaction product mixture with a metal organic salt solution occurs by contacting flowing the halogenation reaction product mixture against a countercurrent flow of the metal organic salt.

In some embodiments, the inventive method further comprises stripping the bromine from the bromine containing gasses and recycling the bromine into the halogenations reactor.

In certain embodiments of the inventive method, the alkane to halogen gas molar ratio is greater than 2:1. All individual values and subranges greater than a 2:1 ratio are included herein and disclosed herein; for example, the alkane to halogen gas molar ration can be from a lower limit of 2:1, 2.2:1, 2.4:1, 2.6:1, 2.8:1, 3:1, 3.5:1, 3.8:1, 4:1; 4.2:1. Ina preferred embodiment the alkane to halogen gas molar ratio is greater than or equal to 4:1.

The halogenations step wherein the alkane and halogen gas are reacted to form an alkane halide and a hydrogen halide is, in some embodiments of the inventive method, autocatalytic following initiation. In such embodiments, the halogenations reaction may be initiated by application of heat to a temperature between 350 and 450° C. All individual values and subranges from 350 and 450° C. are included herein and disclosed herein; for example, the halogenation reaction initiation temperature can be from a lower limit of 350, 360, 370, 380, 390, 400, 410, 420, 430, or 440° C. to an upper limit of 360, 370, 380, 390, 400, 410, 420, 430, 440 or 450° C. For example, the halogenation reaction initiation temperature may be in the range of from 350 to 380° C., or in the alternative, halogenation reaction initiation temperature may be in the range of from 380 to 400° C., or in the alternative, the halogenation reaction initiation temperature may be in the range of from 400 to 450° C.

In alternative embodiments, the halogenations reaction may be initiated at lower temperatures in the presence of ultraviolet radiation. In such embodiments, the halogenations reaction initiation temperature may be in the range from 250 to 350° C. All individual values and subranges from 250 and 350° C. are included herein and disclosed herein; for example, the halogenation reaction initiation temperature can be from a lower limit of 250, 260, 270, 280, 290, 300, 310, 320, 330, or 340° C. to an upper limit of 260, 270, 280, 290, 300, 310, 320, 330, 340 or 350° C. or example, the halogenation reaction initiation temperature may be in the range of from 250 to 280° C., or in the alternative, halogenation reaction initiation temperature may be in the range of from 280 to 300° C., or in the alternative, the halogenation reaction initiation temperature may be in the range of from 300 to 350° C.

Following initiation, in some embodiments of the inventive method, the heat generated by the halogenation reaction is sufficient to maintain the halogenation reaction.

The following description of the drawing is an example of one embodiment of the inventive method and is not intended to the scope of the invention.

Referring to FIG. 1, natural gas comprising methane enters a mixing chamber 1 through line 2 in which it is mixed with bromine vapor entering mixing chamber 1 through line 3. The natural gas/bromine vapor mixture passes into the halogenations reactor 5 wherein methyl bromide and hydrobromic acid are formed. The halogenations reaction product mixture which may further comprise unreacted gasses passes through line 6 to condenser 7 wherein the mixture is cooled. Following cooling the halogenation reaction product mixture is passed through line 8 and flowed upward into extractor 9 through an inert packing material 10 (not shown) against a counterflow of magnesium formate solution which enters extractor 9 through line 38. Magnesium bromide is formed and magnesium bromide solution exits extractor 9 through line 11. Also formed in extractor 9 is methyl formate and formic acid gasses which exit extractor 9 through line 12. Magnesium bromide solution enters reactor 13 wherein it is heated and reacted with oxygen entering through line 16. Bromine containing gasses are led from reactor 13 through line 17 to cooler 18 where most of the bromine is recovered and exits cooler 18 through line 19. Gasses containing traces of bromine are led from cooler 18 to absorber 20 through line 21 wherein the gasses are contacted with a counterflow of solvent, thereby recovering the remainder of the bromine. Bromine free gasses may be vented or otherwise routed through line 22. The bromine containing solvent exits the bottom of absorber 20 and enters the top of stripper 23 through line 24. In the stripper 23, the bromine containing solvent is contacted with methane entering the stripper 23 through line 39, thereby stipping the bromine from the bromine containing solvent. Stipped solvent may be recovered from the bottom of stipper 23 and pumped using pump 26 through line 28 into the top of absorber 20. Magnesium oxide from oxidation reactor 13 enter reactor 29 through line 30. Water is added to reactor 29 through line 31. A slurry of magnesium oxide is formed in reactor 29 and is passed through line 32 into the top of stripper 33 wherein the magnesium oxide slurry is contacted with a counterflow of methyl formate and formic acid gasses. In stripper 33, methanol is formed and exits stripper 33 to condenser 34. Condenser 34 cools the methanol which is collected through line 35. Gas products of stripper 33 which are substantially free of methanol are passed into mixing chamber 1 through line 36. Magnesium formate solution leaves stripper 33 through line 38 through which it is passed into extractor 9.

The present invention may be embodied in other forms without departing from the spirit and the essential attributes thereof, and, accordingly, reference should be made to the appended claims, rather than to the foregoing specification, as indicating the scope of the invention.

We claim:

1. A method comprising
reacting an alkane gas with a halogen gas in a halogenation reactor to form a halogenation reaction product mixture comprising alkane halide and hydrogen halide mixture;
contacting the halogenation reaction product mixture with a metal organic salt thereby forming an extractor product mixture of a metal halide, organic ester, and organic acid;
separating the organic ester and organic acid mixture from the metal halide;
oxygenating the metal halide to form a metal oxide and halide containing gasses;
separating the metal oxide from the halide containing gasses;
mixing the metal oxide with water to form a metal oxide slurry;
mixing the metal oxide slurry with a countercurrent flow of the organic ester and
organic acid mixture to form a raw product comprising alkanol, a metal organic salt.

2. The method of claim 1 wherein the alkane gas is selected from the group consisting of methane, ethane, propane and mixtures thereof.

3. The method of claim 1 wherein the halogen gas is selected from the group consisting of chlorine gas, bromine gas, and iodine gas.

4. The method of claim 1 wherein the metal organic salt is selected from the group consisting of metal formate, metal acetate, metal benzoate, and combinations thereof.

5. The method of claim 1 wherein the organic acid is selected from the group consisting of substituted or nonsubstituted aliphatic or aromatic organic acids.

6. The method of claim 1 wherein the metal is selected from Magnesium, Zinc, and combinations thereof.

7. The method of claim 1 wherein the alkane is methane, the metal organic salt is magnesium formate, the halide gas is selected from the group consisting of bromine gas, chlorine gas, and mixtures thereof, and the alkanol is methanol.

8. The method of claim 1 wherein the alkane is ethane, the metal organic salt is magnesium formate, the halide gas is selected from the group consisting of bromine gas, chlorine gas, and the alkanol is ethanol.

9. The method of claim 1 wherein the alkane is methane, the metal organic salt is magnesium acetate, the halide gas is selected from the group consisting of bromine gas, chlorine gas, and mixtures thereof, and the alkanol is methanol.

10. The method of claim 1 wherein the alkane is ethane, the metal organic salt is magnesium acetate, the halide gas is selected from the group consisting of bromine gas, chlorine gas, and the alkanol is ethanol.

11. The method of claim 1 wherein the alkane is methane, the metal organic salt is magnesium benzoate, the halide gas is selected from the group consisting of bromine gas, chlorine gas, and mixtures thereof, and the alkanol is methanol.

12. The method of claim 1 wherein the alkane is ethane, the metal organic salt is magnesium benzoate, the halide gas is selected from the group consisting of bromine gas, chlorine gas, and the alkanol is ethanol.

13. The method of claim 1 wherein the step of contacting the halogenations reaction product mixture with the metal organic salt occurs in by flowing the halogenations reaction product against a countercurrent flow of the metal organic salt in a column packed with an inert packing material.

14. The method of claim 1 further comprising stripping the bromine from the bromine containing gasses and recycling the bromine into the halogenations reactor.

15. The method of claim 1 wherein the alkane to halogen gas molar ratio is greater than 2:1.

16. The method of claim 1 wherein the alkane to halogen gas molar ratio is equal to or greater than 4:1.

17. The method of claim 1 wherein the reaction of the alkane and the halogen gas is initiated by application of heat to a temperature of 350 to 450° C.

18. The method of claim 1 wherein the reaction of the alkane and the halogen gas is initiated by application of heat to a temperature of 250 to 350° C. in the presence of ultraviolet radiation.

19. The method of claim 1 wherein the oxygenating the metal halide occurs in a fluidized bed reactor.

* * * * *